(12) United States Patent
Shoji et al.

(10) Patent No.: US 8,123,925 B2
(45) Date of Patent: Feb. 28, 2012

(54) ELECTROPHORETIC APPARATUS

(75) Inventors: Tomohiro Shoji, Hitahinaka (JP); Jin Matsumura, Hitachinaka (JP); Hidenori Namba, Naka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1133 days.

(21) Appl. No.: 11/984,719

(22) Filed: Nov. 21, 2007

(65) Prior Publication Data
US 2008/0116073 A1 May 22, 2008

(30) Foreign Application Priority Data
Nov. 22, 2006 (JP) ................... 2006-314972

(51) Int. Cl.
*G01N 27/453* (2006.01)
(52) U.S. Cl. .................. 204/604; 204/453; 204/605
(58) Field of Classification Search .............. 204/453, 204/455, 604.605
See application file for complete search history.

(56) References Cited

U.S. PATENT DOCUMENTS

| | | | | | |
|---|---|---|---|---|---|
| 3,888,460 | A | * | 6/1975 | Sigmon | 251/315.05 |
| 5,173,163 | A | * | 12/1992 | Tehrani | 204/452 |
| 5,635,050 | A | * | 6/1997 | Pentoney et al. | 204/605 |
| 5,963,456 | A | | 10/1999 | Klein et al. | |
| 6,352,633 | B1 | * | 3/2002 | Liu et al. | 204/453 |
| 2004/0035702 | A1 | * | 2/2004 | Kawazoe et al. | 204/452 |
| 2007/0205105 | A1 | | 9/2007 | Kawazoe et al. | |

FOREIGN PATENT DOCUMENTS

| | | |
|---|---|---|
| JP | 01-142237 A | 6/1989 |
| JP | 04-081637 A | 3/1992 |
| JP | 07-044977 U | 12/1995 |
| JP | 2001-281221 | 10/2001 |
| JP | 2001-324473 | 11/2001 |
| JP | 2001-324475 | 11/2001 |
| JP | 2004-085292 A | 3/2004 |

OTHER PUBLICATIONS

Japanese Office Action issued in Japanese Patent Application No. 2006-314972, dated Jul. 26, 2011.

* cited by examiner

*Primary Examiner* — Kaj K Olsen
(74) *Attorney, Agent, or Firm* — McDermott Will & Emery LLP

(57) ABSTRACT

An electrophoretic apparatus that allows bubbles to be readily removed out of an electrophoretic passage. The passage for electrophoretic medium, at a connecting section where capillaries filled with electrophoretic medium are connected with a pumping mechanism for filling the electrophoretic medium, is arranged such that the side of the pumping mechanism is disposed below the side of the capillaries, so that the electrophoretic medium flows from down to up at the connecting section when filling the electrophoretic medium into the capillaries. Preferably, the passage between the capillary array and the buffer solution is controlled by using a rotary-type valve having high withstand pressure to simplify the passage structure. The dead volume of the passage can be reduced and the valuable electrophoretic medium can be efficiently used. The amount of used electrophoretic medium required for the removal of the bubble can be also reduced.

5 Claims, 4 Drawing Sheets

FRONT CROSS SECTION

SIDE CROSS SECTION

ELECTROPHORETIC APPARATUS

CLAIM OF PRIORITY

This application claims the benefit of Japanese Patent Application No. JP 2006-314972, filed on Nov. 22, 2006, the disclosure of which is incorporated herein by reference.

BACKGROUND OF THE INVENTION

1. Field of the Invention

The present invention relates to a capillary electrophoretic apparatus. More specifically, the invention relates to an electrophoretic apparatus that requires replacement or attachment of capillaries or a capillary array and that requires air to be removed out of a connecting section between the capillaries or the capillary array and the electrophoretic apparatus or out of passages that become electrophoretic passages.

2. Background Art

Capillary electrophoresis is now widespread as a technology for separating and analyzing many biological samples including deoxyribonucleic acid (DNA). One of technological advantages thereof is its excellent heat-radiating characteristic brought about by the surface-area to volume ratio of a capillary. This heat-radiating characteristic enables high-speed and high-resolution sample separation by electrophoresis using high voltage.

Capillary electrophoresis also has a feature that multiple analyses can be readily carried out using a large number of capillaries at the same time. A multiple-capillary type high-throughput electrophoretic apparatus has been put into practical use.

JP Patent Publication (Kokai) Nos. 2001-281221 A, 2001-324473 A, and 2001-324475 A disclose electrophoretic apparatuses using a capillary array composed of 16 capillaries.

A capillary is a fine tube having an inner diameter of several ten to several hundred microns. Its main material is quarts and polyimide of around several ten microns in thickness is coated around the outside of the quarts to enhance its mechanical strength. During electrophoresis, the capillary is filled with a component that becomes sample-separating medium.

Although non-fluid cross-linking polymer has been once used as the sample-separating medium, a non-cross-linking fluid polymer that excels in terms of productivity and performance stability is now the mainstream. JP Patent Publication (Kokai) No. 2001-281221 A discloses a pumping mechanism for filling gel, i.e., sample-separating medium, into capillaries. Although it discloses a glass syringe as the pumping mechanism, there also exists an electrophoretic apparatus that has a pumping mechanism for driving a sapphire plunger other than the glass syringe.

Furthermore, JP Patent Publication (Kokai) No. 2001-324473 A has disclosed a method of changing the length or number of capillaries corresponding to the type of analysis or a throughput required by a user. For example, relatively long capillaries are used in applications that require high resolution of distinguishing differences of length of one base of DNA from around several hundreds to thousand bases. Furthermore, relatively short capillaries are used when an analysis needs to be carried out quickly even if the resolution drops more or less. While a large-scale user such as a large-scale gene analysis center who handles a large number of samples at the same time requires a high throughput, a small-scale user on the level of laboratory often requires only a low throughput.

JP Patent Publication (Kokai) No. 2001-324475 A discloses a capillary array in a mode replaceable by the user. It is arranged so as to press down the capillary array at three points of a sample introducing end, an optical detecting section, and a polymer solution-supplying end. The polymer solution-supplying end of the capillary array is connected to a pumping mechanism of the electrophoretic apparatus.

More specifically, in the electrophoretic apparatuses disclosed in JP Application (Kokai) Nos. 2001-281221 A, 2001-324473 A, and 2001-324475 A, the polymer solution supplying end is arranged so that 16 capillaries are put into a bundle of around 3.5 mm in diameter that is inserted into an acrylic block in a horizontal direction and sealed and connected by a sleeve and a push screw. A syringe for a reservoir for storing polymer solution and an injection syringe for injecting the polymer solution into the capillaries at high pressure are attached to the block. The both syringes communicate with the capillary array via passages within the block. Furthermore, the electrophoretic apparatus has a second block to which a container for storing buffer solution can be attached. The first block to which the capillary array is attached is connected with the aforementioned second block by a tube. The capillary array communicates with the buffer solution provided in the second block through the passage formed in the first passage, the tube and a passage formed in the second block. An electrode that becomes an anode side is soaked into the buffer solution provided in the second block, so that the passage from the capillary array to the buffer solution becomes an electrophoretic passage to which voltage is applied during electrophoresis.

Because high voltage of several to several ten kilovolts is applied across the both ends of the electrophoretic passage in the electrophoretic apparatus, there is a possibility of causing discharge or the like if air is mixed into the electrophoretic passage. Because a section for connecting the capillary array with the electrophoretic apparatus is a part of the electrophoretic passage, bubbles must be reliably removed out of the connecting section in installing the capillary array to the electrophoretic apparatus.

In the apparatuses described above, the user removes the bubbles in installing the capillary array to the electrophoretic apparatus. The removal of the bubbles is normally carried out by moving a plunger of either glass syringe to supply the polymer solution to the passage and by discharging the bubbles together with the polymer solution out of a discharge port provided in the second block.

As a result of ardent study by the inventors of the present application, it was found that the ease of replacement of the capillary array is an important point when users evaluate controllability of the electrophoretic apparatus. The inventors also found that readiness of removal of air mixed in the passage in installing the capillary array largely influences the ease of replacement of the capillary array.

The diameter of the passages in the first and second blocks and the tube is as small as around 1 mm so that the removal of bubbles may be readily carried out. However, the larger the diameter of the capillary or the more the number of capillaries, the wider the space of the connecting section for connecting the capillary array with the electrophoretic apparatus becomes in order to accommodate the diameter (about 3.5 mm in case of 16 capillaries) of the bundle of the capillary array. The polymer solution flows from up to down in this part. The polymer solution flows in a direction opposite from a direction in which the bubbles within the polymer solution float up. Therefore, the solution flows locally within the space if the space of the connecting section is wide and the bubbles cannot be easily removed out just by moving the plunger to supply the polymer solution to the passage. There is even a case of consuming a large amount of valuable polymer solution due to the bubbles remaining in the capillary array connecting section.

In view of the problems described above, it is an object of the present invention to provide an electrophoretic apparatus that allows bubbles to be readily removed out of the electrophoretic passage.

SUMMARY OF THE INVENTION

In accordance with the invention, electrophoretic medium flows from down to up in a connecting section where capillaries into which the electrophoretic medium is filled is connected with a pumping mechanism for filling the electrophoretic medium.

Furthermore, a passage between the capillary array and buffer solution is controlled preferably by using a rotary-type valve having a high pressure resistant characteristic to simplify the passage structure. It allows a dead volume in the passages to be reduced and the valuable electrophoretic medium to be used efficiently. The amount of the electrophoretic medium required for removing the bubbles can be also reduced.

Furthermore, the invention relates to a passage structure in which the passage is preferably extended from the buffer to a certain position that becomes an apex thereof and in which a valve is disposed on the way of the passage. Because the passage positioned below the apex is replaced by the buffer solution that is lighter than the electrophoretic medium, the electrophoretic medium is replaced with the buffer solution also in the valve on the way of the passage. Thus, the time during which the valve contacts the electrophoretic medium is shortened, thus prolonging the life of the valve and improving the reliability.

EFFECTS OF THE INVENTION

The present invention allows bubbles to be readily removed out of the electrophoretic passages in installing the capillary array to the electrophoretic apparatus and thus improves the controllability of the electrophoretic apparatus.

DESCRIPTION OF PREFERRED EMBODIMENTS OF THE INVENTION

Figure 1:
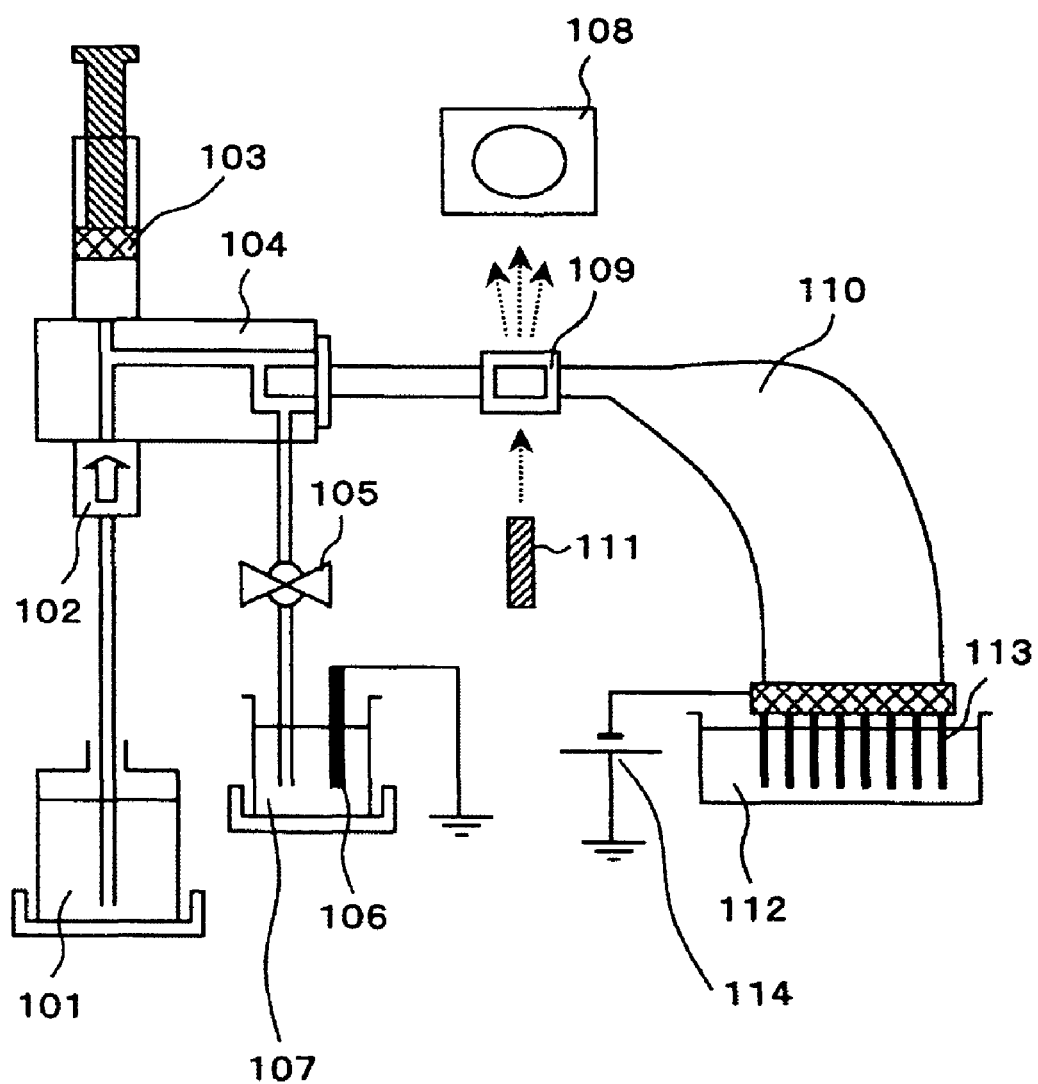
FIG. 1 is a schematic diagram showing a basic structure of an electrophoretic apparatus having a polymer injecting mechanism.

FIG. 1 is a schematic diagram showing a basic structure of a capillary electrophoretic apparatus. The capillary electrophoretic apparatus has a capillary electrophoretic section including capillaries (fine tubes of several tens to several hundreds micron in diameter) filled with high viscous polymer solution (referred to as polymer hereinafter) that is electrophoretic medium, and an optical detecting section for detecting electrophoretically separated sample. The capillary electrophoretic apparatus also includes a passage block 104 composing a connecting passage for connecting with the capillaries, and a polymer injecting mechanism communicating with the connecting passage that is a pump for filling the electrophoretic medium into the capillaries. When the pump 103 is manipulated, the polymer injecting mechanism performs operations of taking in the polymer from a bottle (referred to as a polymer bottle hereinafter) 101 in which the polymer is stored and of injecting the polymer into the capillary array composed of 16 capillaries for example. The polymer injecting mechanism is used also in removing bubbles within the passage block 104.

An outline of the apparatus will now be explained. One end (sample injecting end) of the capillary array 110 having the 16 capillaries is soaked into buffer within a buffer container 112, and the other end is connected to the passage block 104. Beside the capillary array 110, the passage block 104 is connected with the pump 103, the polymer bottle 101 storing the polymer to be injected into the capillaries and another buffer container 107. Passages communicating them are formed in the block. A check valve 102 is disposed between the passage block 104 and the polymer bottle 101 to prevent the polymer from flowing back to the polymer bottle 101 in injecting the polymer from the pump 103 into the capillaries of the capillary array 110.

The polymer bottle 101 used here is one having an enough capacity for continuous operation. The polymer bottle 101 is constructed so as to have an enough gap around its exhaust valve or tube inserting port so that no negative pressure is created within the bottle even if the polymer is taken out. Furthermore, the polymer bottle 101 is disposed at position lower than the buffer container 107 so that no polymer flows back from the polymer bottle 101 to the side of the buffer container 107 due to pressure caused by difference of height. At this time, the check valve 102 prevents the polymer or the buffer solution from flowing into the polymer bottle 101.

An electric buffer valve 105 is disposed between the buffer container 107 and the passage block 104. The buffer valve 105 is closed when the polymer is injected into the capillaries of the capillary array 110 to close the passage between the capillary array and the buffer container. The buffer valve 105 is opened during electrophoresis to open the passage and to communicate the capillary array with the buffer container.

Figure 2:
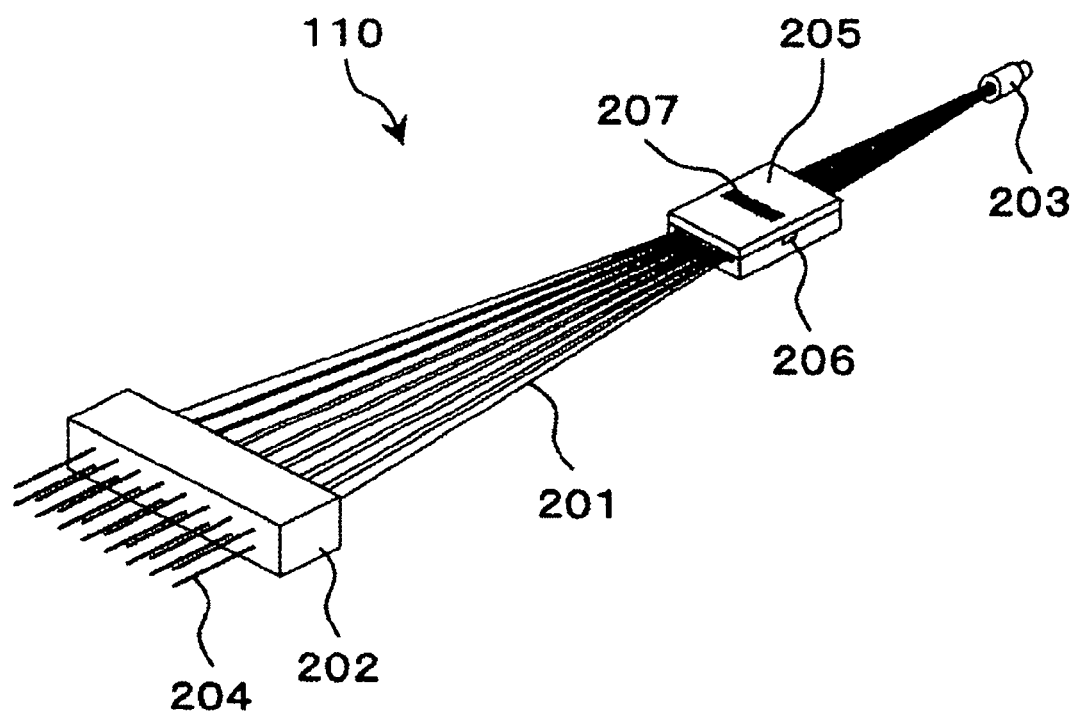
FIG. 2 is a schematic diagram showing a basic structure of a capillary array.

FIG. 2 is a schematic diagram showing one exemplary capillary array 110. Each capillary 201 composing the capillary array has an outer diameter of about 0.1 to 0.7 mm and an inner diameter of about 0.02 to 0.5 mm. Its outer surface is coated with polyimide resin. The capillary itself is a quarts pipe and the capillary array is composed of a plurality of arrayed capillaries (16 in this example). The capillary array 110 has a load header 202 for taking in the samples from the sample container storing fluorescent-labeled DNA samples and the like by an electrical action, a detecting section (window unit) 205 for arraying and fixing the capillaries 201 in order of Nos. of samples in the load header 202, and a capillary head 203 where the capillaries are bundled and bonded. Hollow electrodes 204 for applying electrophoretic voltage to the capillaries are provided at the sample-injecting end projecting from the load header 202. The detecting section (window unit) 205 has an opening 206 for irradiating light to the aligned capillary array from the side thereof and an opening 207 for taking out light emitted from the capillaries.

The shape of the capillary head 203 of the capillary array, i.e., the shape of the section connecting with the passage block 104, may be planar in which the capillaries are arrayed in a row or round in which the capillaries are put together as one bundle; the shape, however, is not limited to those. In case of the round type, the capillary head 203 may be installed to the passage block 104 by attaching a sleeve to the capillary head 203, fastening a push screw from behind, and filling up the gap by deforming the sleeve.

The hollow electrode 204 projecting out of the load header 202 and the sample injecting ends of the capillaries 201 of the capillary array 110 shown in FIG. 2 are soaked into a sample tray having a plurality of wells storing the fluorescent-labeled DNA samples and the other end of the capillary head 203 is pressure-tightly attached to the passage block 104 filled with the polymer. A high voltage of several kV is applied from a high voltage power source 114 to an electrode 106 soaked into the buffer container 107 that is connected to the passage block 104 and to the hollow electrode 204 of the load header 202 so that the samples within the sample container are electrolytically injected into each capillary of the capillary array. After that, the sample injecting ends of the capillary array 110 are soaked into the buffer container 112 as shown in FIG. 1, so that the samples electrolytically injected into each capillary are separated by electrophoresis.

Laser light emitted from a laser source 111 is guided by an exciting optical system to the detecting section (window unit) 205 so as to irradiate the capillaries. A photodetector 108 detects fluorescent light that is signal light emitted from the samples migrating within the capillaries by the irradiation of exciting light.

It is noted that the apparatus structure shown here is one concrete example and will not limit the invention.

The capillary array 110 is a replaceable part and one having a different number of capillaries or a different length is used depending on a purpose of use of the user. Furthermore, the capillary array is replaced when it deteriorates due to contamination and the like. Normally, the replacement of the capillary array is carried out by the user. When the capillary array is installed, it is then necessary to remove air mixed into the passage block 104. A trouble such as discharge may occur if the air remains as bubbles because a part of passages within the passage block, particularly the passage between the capillary array 110 and the buffer container 107, is a part where voltage is applied. When the apparatus is initially used or when the capillary array is installed (referred to as "install" hereinafter) after cleaning and drying parts composing the passages such as the passage block 104, all the passages including the capillary array connecting section are filled by the polymer. At this time, the polymer is supplied by using the pump 103. In replacing the capillary array by stopping operation of the apparatus, bubbles mixed into the passage block 104 are discharged by causing the polymer to flow from the pump 103. If there is a place where the bubbles remain, the polymer is flown to push out the bubbles by the polymer, so that there is a case of consuming a large amount of valuable polymer as a result. Specifically, the bubbles are discharged as follows in the structure of the embodiment shown in FIG. 1. At first, the capillary array 110 is connected and the buffer valve 105 is opened. The polymer is supplied from the pump 103 to discharge the bubbles together with the polymer from the buffer container side. Normally, the diameter of the passage within the passage block 104 is reduced to about 1 mm so that the bubbles may be readily removed and so that a homogeneous flow occurs within the passage. In contrary, the part connecting the capillary array cannot be readily reduced because a space for accommodating the capillary head 203 is required. Furthermore, it is difficult to push air down because of the nature of air to float up in the polymer when the polymer flows through the capillary array in the direction from up to down as shown in FIG. 1. As a result, this part is one of parts where air is apt to remain most within the passage block 104.

When there is such part where it is difficult to remove the bubbles, there is a case of using a large amount of polymer to remove the bubbles as a result.

Figure 3:
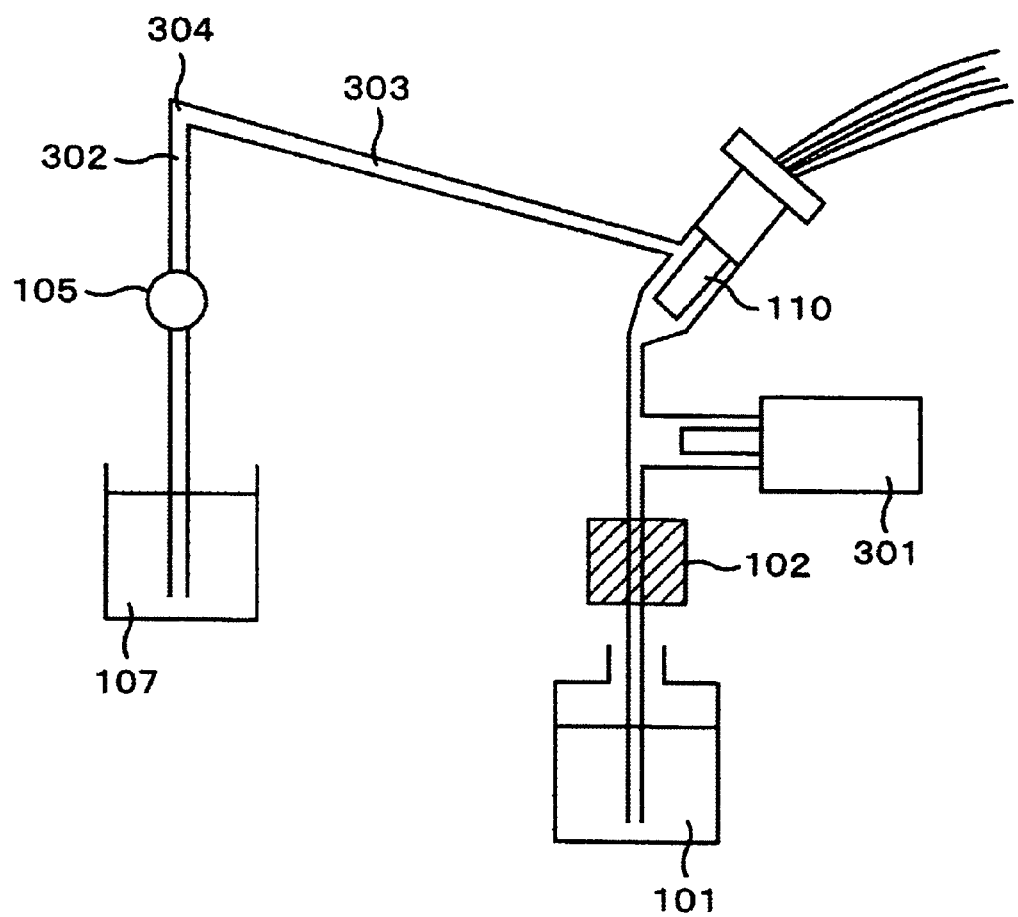
FIG. 3 is a schematic diagram of a passage structure of an embodiment.

FIG. 3 is a schematic diagram of a flow passage structure of an embodiment.

One feature of the structure shown in FIG. 3 is that the capillary array 110 is connected so that it faces obliquely downward and that the passage is arranged so that the polymer is fed from the downside to the capillary array connecting section. The passage of the electrophoretic medium formed by connecting the capillary array and the connecting passage is arranged such that the side of the capillary faces up and the side of the connecting passage faces down. The end face of the capillary connected with the connecting passage faces down. The end face of the capillary is disposed below the part where the passage 303 communicates with the connecting passage. Although the pump 301 is disposed below the capillaries in the figure, this is one of embodiments for explaining the invention and the disposition may be changed in accordance to convenience of apparatus design. For example, the capillary and the pump may be disposed on the same level. The passage 303 communicates with the buffer container 107 via the passage 302 having the buffer valve 105 on its way.

Here, the pump 301 plays the same role with the pump 103 shown in FIG. 1. This disposition pushes up the bubbles in the capillary array connecting section from the down side by the polymer and discharges the bubbles to the upper passage 303. That is, this is a behavior conforming to the nature that the bubbles flow up in the polymer, so that the air may be readily discharged out of the capillary array connecting section. Thereby, economy of the apparatus improves because the convenience of use of the apparatus improves and a consumed amount of the polymer required in removing the bubbles may be reduced as a result.

The apex 304 is provided between the buffer valve 105 and the capillary array 110. The passage bends so as to have at least one apex, the apex is positioned above the level of the buffer solution, and the valve for opening/closing the passage is provided at the part located between the apex and the level of the buffer solution.

Figure 4:
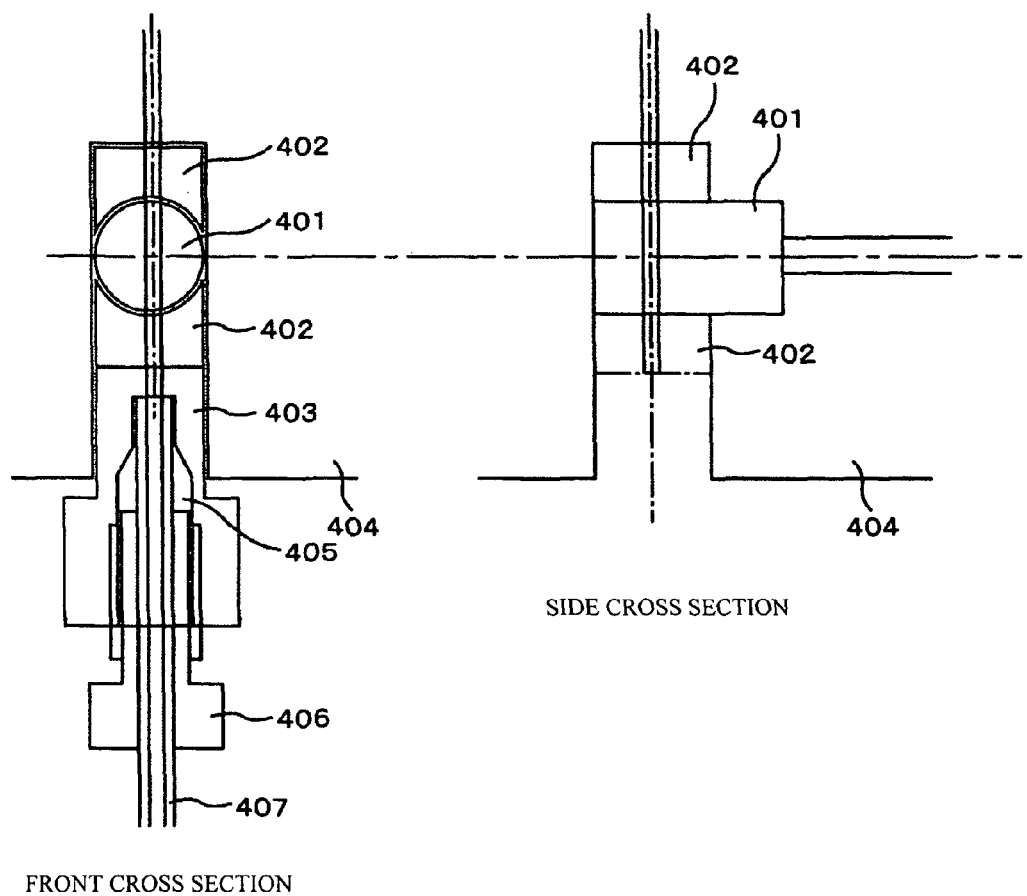
FIG. 4 is a schematic diagram of a rotary-type valve of the embodiment.

When the passage whose diameter is around 1 mm and into which the polymer is filled is soaked into the buffer solution, replacement occurs between the polymer within the passage and the buffer solution due to a difference of density of the polymer and the buffer solution (normally the buffer solution is lighter). That is, when the buffer container 107 is attached after filling the polymer into all the passages in the structure shown in FIG. 3, the polymer within the passage 302 and the buffer valve 105 located on the way of the passage 302 is replaced with the buffer solution. One concern of using a rotary-type valve as shown in FIG. 4 in the electrophoretic apparatus is that components of the valve may be damaged by crystallized polymer. Although one of features of this arrangement is that the internal rotor 401 and the stators 402 may be readily replaced as described before, it is better to be able to use them for a long period of time without being damaged and without being replaced. The inside of the valve is filled not with the polymer that is liable to be crystallized but with the buffer solution that is hardly crystallized in the structure shown in FIG. 3, so that the risk of damaging the components sharply decreases. That is, it prolongs the lives of the components and enhances their reliability. When the replacement of the polymer with the buffer solution advances and the buffer solution reaches to the capillary array 110, the buffer solution is injected to the capillary array instead of the polymer in trying to inject the polymer into the capillary array. Therefore, it is necessary to avoid this from happening.

In the structure shown in FIG. 3 however, the replacement of the polymer and the buffer solution stops at the apex 304. This is because the passage 303 is oriented in the direction descending from the apex 304 so that the buffer solution will not advance to the passage 303 going against the polymer. It becomes possible to prevent the buffer solution from mixing into the capillary array and to prolong the life of the rotary valve by providing the position that becomes the apex between the buffer valve and the capillary array.

The structure of the buffer valve 105 of the present embodiment will be explained with reference to FIG. 4. FIG. 4 is a schematic diagram showing the rotary-type valve used as the buffer valve. The rotary-type valve includes a rotor 401, stators 402 for sandwiching the rotor 401, and a push screw 403 for pressing down the rotor 401 and the stators 402. The passage is opened/closed as the inner rotor 401 turns. The stator 402 in the figure is a stator that closely contacts with the rotor 401 without turning. The two stators 402 are built into a supporting body 404 so as to sandwich one rotor 401 and the push screw 403 presses down the respective parts from each other. The passage may be extended by arbitrary length to a spot by connecting a tube 407 composing the passage, a sleeve 405 for sealing the tube and a push screw for closely bonding the tube by crashing the sleeve. A feature of this structure is that a degree of tightness of the rotor 401, the stators 402 and the supporting body 404 is adjustable by the push screw 403 depending on how much it is fastened. Normally, the electrophoretic apparatus requires high pressure of several MPa in order to inject the high viscous polymer solution into the capillaries of several to several tens micron in inner diameter in a short time. In this case, the withstand pressure of the buffer valve must be enhanced to be more than the injecting pressure. Although the small rotary-type valve that controls the opening/closing of the passage by turning the rotor inside may be inserted into the passage and is effective in simplifying the passage structure, there has been no rotary-type valve having the withstand pressure of several MPa that can be used as the buffer valve of the capillary electrophoretic apparatus. In the structure of the embodiment, the two stators sandwich the rotor and the push screw presses down them as described above to enhance the tightness of the components and to realize the high withstand pressure. Another preferable feature is that the internal components can be accessed by removing the push screw 403 so that, when an internal component is damaged by wear or the like, it may be readily replaced.

What is claimed is:

1. A capillary electrophoretic apparatus, comprising:
   one or more capillaries in which electrophoretic medium is filled;
   a first connecting passage that can be connected with the one or more capillaries;
   a pump that communicates with the first connecting passage and that can fill the electrophoretic medium into the one or more capillaries;
   a second connecting passage that communicates with the connecting passage,
   a buffer container that communicates with the second connecting passage and stores buffer solution into which an electrode for applying voltage to the electrophoretic medium is soaked; and
   a valve provided in the second passage,
   wherein:
   an end face of the one or more capillaries connected with the first connecting passage faces downward and is positioned below a part where the second connecting passage communicates with the first connecting passage.

2. The electrophoretic apparatus according to claim 1, wherein the valve has a rotor, stators for sandwiching the rotor, and a push screw for pressing down the rotor and the stators.

3. The electrophoretic apparatus according to claim 1, wherein the valve is a rotary-type valve.

4. A capillary electrophoretic apparatus, comprising:
   one or more capillaries in which electrophoretic medium is filled;
   a first connecting passage that can be connected with the one or more capillaries;
   a pump that communicates with the first connecting passage and that can fill the electrophoretic medium into the one or more capillaries;
   a second connecting passage that communicates with the connecting passage,
   a buffer container that communicates with the second connecting passage and stores buffer solution into which an electrode for applying voltage to the electrophoretic medium is soaked,
   wherein:
   an end face of the one or more capillaries connected with the first connecting passage faces downward and is positioned below a part where the second passage communicates with the first connecting passage,
   the second connecting passage is bent so as to have at least one apex that is positioned above the level of the buffer solution, and
   a valve for opening/closing the second connecting passage is provided at position between the apex and the level of the buffer solution in the second connecting passage.

5. The electrophoretic apparatus according to claim 4, wherein the valve is a rotary-type valve.

* * * * *

UNITED STATES PATENT AND TRADEMARK OFFICE
CERTIFICATE OF CORRECTION

PATENT NO. : 8,123,925 B2  Page 1 of 1
APPLICATION NO. : 11/984719
DATED : February 28, 2012
INVENTOR(S) : Tomohiro Shoji et al.

It is certified that error appears in the above-identified patent and that said Letters Patent is hereby corrected as shown below:

Title Page, In Item "(75) Inventors", the address of the first inventor should read --Hitachinaka-- rather than "Hitahinaka".

Signed and Sealed this
Seventeenth Day of December, 2013

Margaret A. Focarino
*Commissioner for Patents of the United States Patent and Trademark Office*